(12) United States Patent
Nguyen

(10) Patent No.: US 6,254,537 B1
(45) Date of Patent: Jul. 3, 2001

(54) FETAL OUTCOME PREDICTOR AND MONITORING SYSTEM

(75) Inventor: Duong Nguyen, Denver, CO (US)

(73) Assignee: Rose Biomedical Development Corporation, Denver, CO (US)

( * ) Notice: Subject to any disclaimer, the term of this patent is extended or adjusted under 35 U.S.C. 154(b) by 0 days.

(21) Appl. No.: 09/398,178

(22) Filed: Sep. 17, 1999

(51) Int. Cl.[7] .................................................. A61B 5/00
(52) U.S. Cl. ........................ 600/300; 600/304; 128/920
(58) Field of Search .................................. 600/300–304, 600/481–486, 500–511, 529–538, 586–588; 128/900, 920–925; 705/2–4

(56) References Cited

U.S. PATENT DOCUMENTS

| | | | |
|---|---|---|---|
| 5,609,156 | * 3/1997 | Keith et al. | 128/925 |
| 5,817,035 | * 10/1998 | Sullivan | 600/588 |
| 5,935,061 | * 8/1999 | Acker et al. | 600/304 |
| 5,957,855 | * 9/1999 | Oriol et al. | 600/511 |

OTHER PUBLICATIONS

Bozoki, Zsolt, "Instruments and Methods: Digital Communication with Fetal Monitors" *Obstetrics & Gynecology*, vol. 90, No. 5, Nov. 1997, pp. 837–839.

Dawes, G.S., Moulden, M. and Redman, C.W.G., Criteria for the Design of Fetal Heart Rate Analysis Systems,, *Int J Biomed Comput*, 1990;25: pp. 287–294.

Dawes, G.S., Moulden, M., and Redman, C.W.G., "Short-Term Fetal Heart Rate Variation, Decelerations, and Umbilical Flow Velocity Waveforms Before Labor", *Obstetrics & Gynecology*, vol. 80, No. 4, Oct. 1992, pp. 673–678.

* cited by examiner

*Primary Examiner*—Robert L. Nasser
*Assistant Examiner*—Michael Astorino
(74) *Attorney, Agent, or Firm*—Gibson, Dunn & Crutcher LLP

(57) ABSTRACT

A fetal health assessor and outcome predictor and monitoring system includes a system for automatically assessing fetal health and predicting fetal outcomes based on fetal and maternal data. The system includes a case-based reasoning processor for categorizing the fetus into one of a plurality of cases based on biographical data about the fetus and mother. The system also includes a transducer for converting physical conditions of the fetus and mother (e.g. characteristics based on heart rates and uterine contractions) to signals representative of the conditions. A computer processor converts the signals to a set of signal features. An assessor and predictor receives the processed signal features and assesses fetal health and predicts fetal outcome based on identified fuzzy relationships between fetal and maternal data and fetal outcomes.

37 Claims, 3 Drawing Sheets

Link between the IFMS and any existing EFM unit.

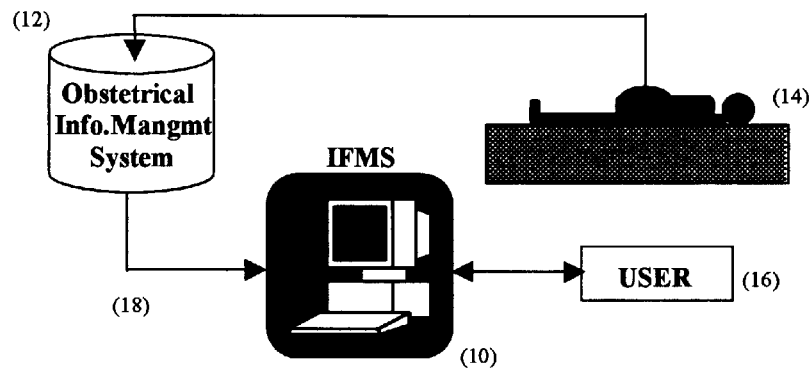
Figure 1: Link between the IFMS and any existing EFM unit.
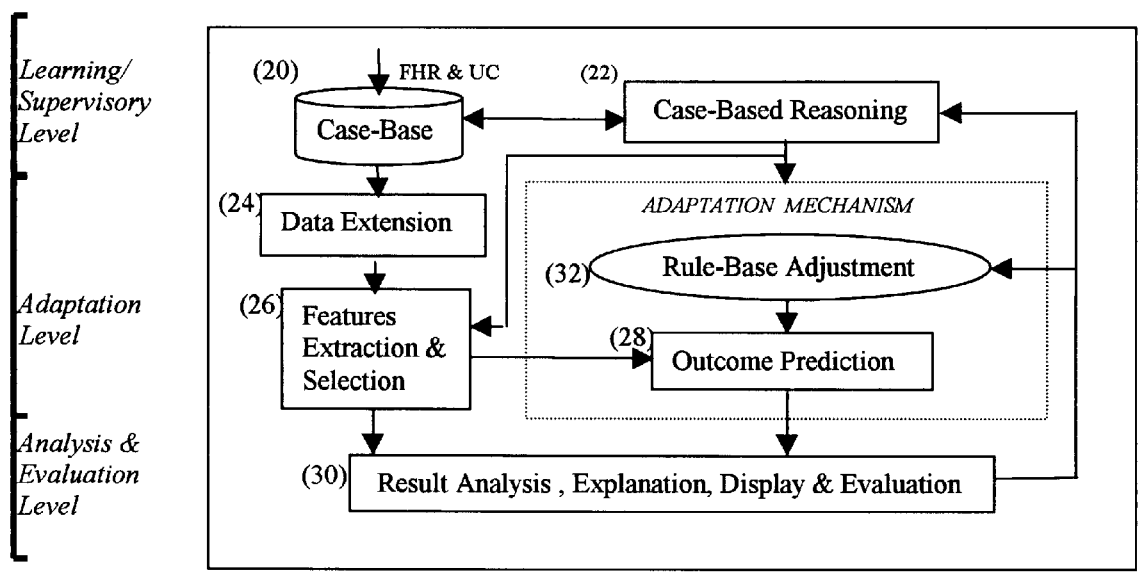
Figure 2: Overall IFMS system architecture

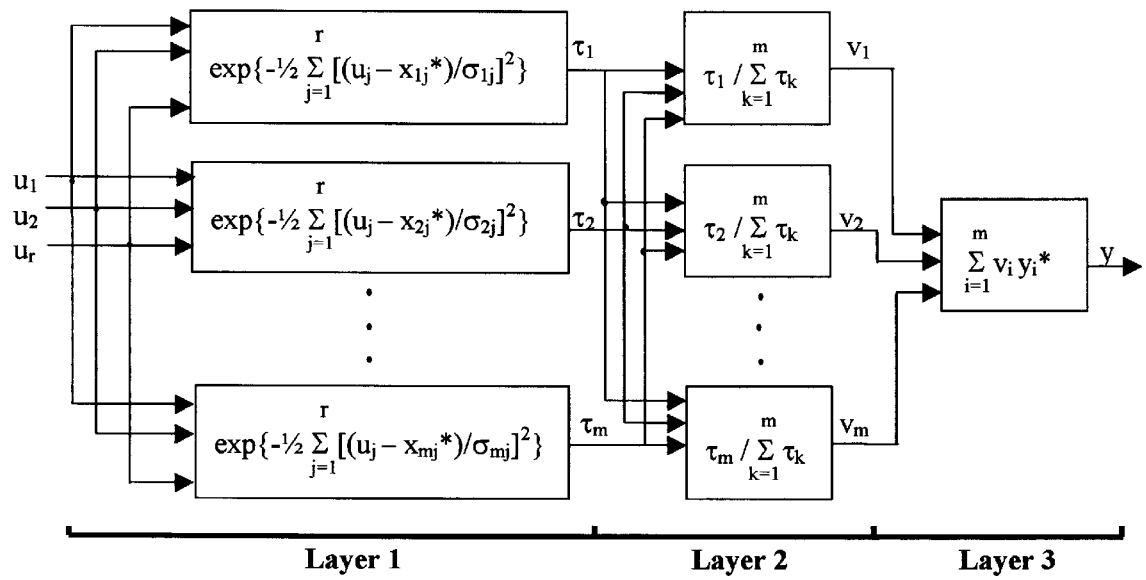
Figure 3 : A three-layer network representation of a linguistic model for fuzzy rules in the Case-Base.
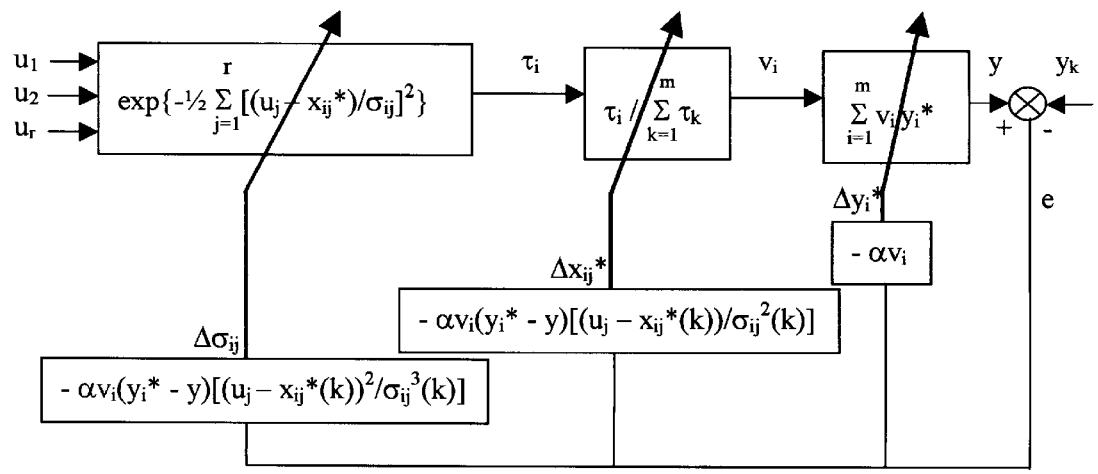
Figure 4 : Learning algorithm for a three-layer fuzzy network

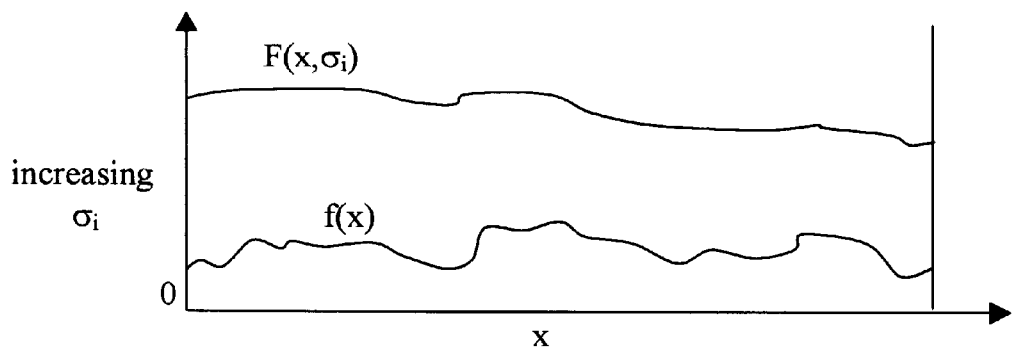
Figure 5: Signal behavior under Gaussian convolution.
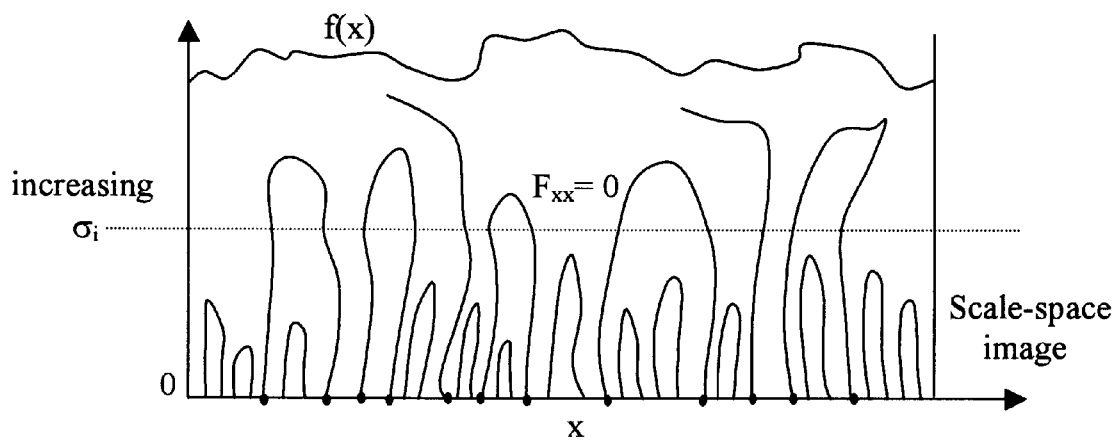
Figure 6: Zero-crossing contours in scale-space image.
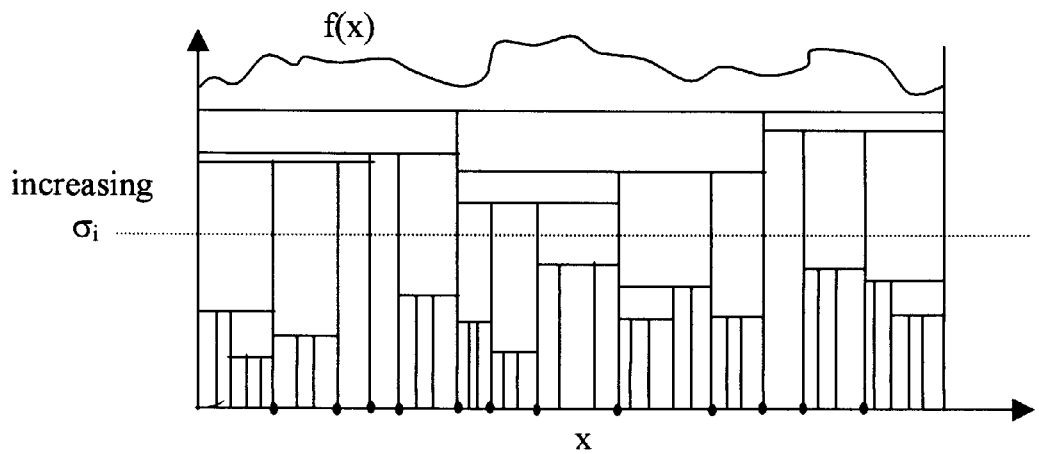
Figure 7: Creation of interval-tree for the results in Figure.6

FETAL OUTCOME PREDICTOR AND MONITORING SYSTEM

The present invention relates to health care, and more particularly, to a method and system for monitoring fetal health and for predicting fetal outcomes based on data about the mother and the fetus.

BACKGROUND OF THE INVENTION

With the continuously escalating cost of health care, one significant issue is balancing the cost of health care versus the quality of health care. While some percentage of health care dollars are wasted on dubious or inappropriate care, it is also true that, even in the United States, there is still preventable disease and death that occurs. The question is how to assure the highest possible quality of care without incurring excessive costs.

One area of health care where the cost-quality debate rages is in the care of pregnant women, where the intent is to deliver healthy babies while preserving the health of the mother. Current national health objectives have targeted reductions in the following areas: infant deaths (before, during, and after birth); low birth weight; severe complications of pregnancy; and instances of severe mental retardation. Current obstetrical practices include: identifying risk factors; monitoring fetal heart rate and maternal uterine contractions (with a Doppler ultrasound device and a tocodynamometer, respectively); ultrasound measurements; amniocentesis; and other laboratory tests which were virtually unknown twenty years ago. Unfortunately, the use of these various monitoring and measurement methods have not significantly improved infant health. Currently-available methods for categorizing pregnancies as healthy or potentially at risk do not appear to be sufficiently accurate and reliable. In addition, since these various monitoring and measurement methods have been implemented, it is believed that the cesarean delivery rate has dramatically increased. While the cesarean delivery rate is now on a slight decline, national health objectives also include a targeted reduction in the cesarean delivery rate.

Much of antepartum care (occurring in physicians' offices from conception until labor) and all of intrapartum care (occurring in the hospital while the patient is in labor) is concerned with the early identification of potentially adverse situations and subsequent early intervention to avoid or minimize adverse events. Yet, there is no highly sensitive and specific technology to assess fetal well-being. A method that accurately and reliably categorizes pregnancies as healthy or potentially at risk is needed to improve perinatal outcomes while managing health care costs.

Typical intrapartum monitoring includes electronic fetal monitoring (EFM) which is often made up of a dual-track strip chart or display of both fetal heart rate (FHR) and uterine contractions (UC). Obstetricians currently determine when it is advisable to intervene (delivering the child by cesarean section as opposed to vaginally) by viewing the EFM data and relying upon their past training and experience. Because of the great uncertainty inherent in this approach, it is natural for obstetricians to seek to err on the side of a cesarean section, which is more likely to result in a safe delivery for a fetus, even though the cesarean section may not have been necessary; is much more costly; and has a potentially greater health impact on the mother. Thus, a much larger number of cesarean sections end up being performed than are necessary. For all of these reasons, a reliable predictor of fetal outcomes would be very useful in assisting obstetricians in determining when it is appropriate to intervene in the delivery process.

Others have proposed systems for automatically assessing fetal health based upon the fetal heart rate. An example of this is disclosed by Dawes, et al., *Int. J. Biomed. Comput.*, 25 (1990) pp. 287–294, "Criteria for the Design of Fetal Heart Rate Analysis Systems," and Dawes, et al., *Obstetrics & Gynecology*, Vol. 80, No. 4, October 1992, pp. 673–678, "Short-term Fetal Heart Rate Variation, Decelerations, and Umbilical Flow Velocity Waveforms Before Labor." The Dawes articles suggest measuring the short-term time variations in the fetal heart rate and determining that the fetal health is in jeopardy when the variations fall below a predetermined threshold. It is believed that such approaches are not sufficiently robust. Furthermore they do not reflect and predict fetal outcomes with sufficient accuracy. It is believed that this lack of robustness is due in part to a lack of any type of artificial intelligence that would allow a system to adapt to and learn about new situations and an inability to accurately assess fetal health from noisy data.

It is against this background, and the desire to solve the problems of and improve on the prior art, that the above invention has been developed.

SUMMARY OF THE INVENTION

The present invention is based upon the belief that EFM data has previously been improperly or incompletely analyzed and interpreted in determining fetal outcomes. The present invention relies upon determining hidden relationships between known EFM data in different scales and known fetal outcomes in past cases for which adequate data are available, and then recognizing characteristics in new EFM data in a current patient that will allow the system to predict the fetal outcome based thereon.

Particularly, the present invention is related to a method of automatically providing an output representative of the health of a fetus carried by a mother, based on fetal and maternal data, with a computer-based predictor. The method includes receiving biographical data about the fetus and the mother and categorizing the fetal and maternal data combination as one of a plurality of types of cases based on the biographical data. The method also includes receiving physical data about the current condition of the fetus and the mother and processing the physical data to extract characteristic features. The method further includes selecting a subset of the characteristic features based on the type of case that the fetal and maternal data combination has been categorized as, and providing an output representative of the health of the fetus from the subset of characteristic features based on previously-developed fuzzy relationships between fetal and maternal data and fetal health.

The method may further include communicating the output to a user. The reported output may be representative of the current status of the fetus. The reported output may be representative of the health of the fetus at a birth that could occur at a predetermined time in the future. The predetermined time may be approximately twenty minutes after the output is reported. The method may further include developing fuzzy relationships between fetal and maternal data and fetal health based on data and known fetal health from past pregnancies and births. The method may further include using the reported fetal health to adjust and optimize the selecting operation. The method may further include using the reported fetal health to adjust and optimize the providing operation.

The present invention is also directed to a method of automatically reporting fetal health for a fetus carried by a mother, based on fetal and maternal data, with a computer-based assessor. The method includes receiving fetal and maternal data and processing the fetal and maternal data to generate and select an optimal set of fetal and maternal features. The method also includes applying the optimal selected set of fetal and maternal features to the assessor to assess and predict fetal health based on identified fuzzy relationships between fetal and maternal data and fetal health.

The method may further include a case-based reasoning processor that receives biographical data about the fetus and the mother and, using case-based reasoning, determines the optimal set of data features to be applied to the assessor. The optimal set of features may be selected based on a learning process that allows the assessor to categorize the fetal and maternal data as belonging to one of a plurality of types of cases and to select the optimal set of features from a larger set of features based on the case type.

The present invention is also directed to a system for automatically assessing fetal health and predicting fetal outcomes based on fetal and maternal data. The system includes a transducer for converting a physical condition of a fetus or mother to a signal representative thereof and a processor for converting the signal to a set of signal features, the set of features being based in part on fetal and maternal biographical data. The system also includes an assessor receptive of the processed signal features for assessing fetal health and predicting fetal outcome based on identified fuzzy relationships between fetal and maternal data and fetal outcomes.

The present invention is also directed to a method of automatically assessing fetal health and predicting fetal outcome based on fetal and maternal data with a computer-based assessor and predictor. The method includes comparing known fetal and maternal data from past pregnancies to the corresponding known fetal outcomes of the past pregnancies and automatically developing inference rules for mapping the known fetal and maternal data to the known outcomes. The method also includes receiving fetal and maternal data for a current pregnancy and automatically applying the developed inference rules to the received fetal and maternal data to assess fetal health and predict a fetal outcome for the current pregnancy.

The comparing operation may also include extracting characteristic signal features from the known data and comparing these extracted features to the known fetal outcomes. The method may further include automatically adjusting the inference rules based on the assessed fetal health and predicted fetal outcome for the current pregnancy.

The present invention is also directed to a method of developing an assessor and predictor for automatically assessing fetal health and predicting fetal outcomes based on fetal and maternal data. The method includes receiving known data from a plurality of births that have already occurred, the known data including fetal and maternal data from a time period prior to and during birth, the known data further including data relating to the health of the fetus immediately after birth, the fetal outcome data. The method also includes processing the known data from the plurality of births to extract signal characteristics and automatically developing inference rules that map the fetal and maternal data from a particular birth from the plurality of births into the fetal outcome data from the particular birth from the plurality of births.

The method may further include using the assessor and predictor to assess fetal health and predict fetal outcomes and automatically adjusting the inference rules based on the assessed fetal health and predicted fetal outcomes.

The present invention is also directed to a method for automatically predicting the future health of a particular person based on present data about the person. The method includes automatically developing inference rules based on known data about persons and known data about the future health of those same persons and receiving physical data about the present status of a particular person. The method also includes automatically processing the received data to generate a set of characteristic features and applying the inference rules to the derived characteristic features to predict the future health of the particular person.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

In the Drawings:

FIG. 1 is a schematic diagram of the environment in which the fetal outcome predictor and monitoring system and method of the present invention can be used.

FIG. 2 is a process flow and block diagram of the various functional blocks of the system and method of the present invention.

FIG. 3 is a block diagram of a three-layer network representation of a linguistic model for fuzzy rules in the Case-Base of the present invention.

FIG. 4 is a block diagram of a learning algorithm for a three-layer fuzzy network used in the present invention.

FIG. 5 is a graphical representation of signal behavior under Gaussian convolution, as employed in the present invention.

FIG. 6 is a graphical representation of zero-crossing contours in scale-space image, as employed in the present invention.

FIG. 7 is a graphical representation of the creation of an interval-tree for the graphical representation of FIG. 6.

DETAILED DESCRIPTION OF THE PREFERRED EMBODIMENTS

The fetal outcome predictor and monitoring system of the present invention includes an Intelligent Fetal Monitoring System (IFMS) 10 as shown in FIG. 1. The IFMS 10 is used in conjunction with an Obstetrical Information Management System (OIMS) 12 that receives, processes, and stores data from a patient, such as an expectant mother 14. A user 16, such as a physician, can use the IFMS 10 to assist in making decisions about the course of treatment to be taken for the expectant mother, such as continuing to wait for a child to be delivered vaginally or whether to intervene and deliver the child by cesarean section. The IFMS 10 can be used in a physician's office prior to the mother entering labor, or can be used once a mother has entered labor whether in a physician's office, at the hospital, or elsewhere. The IFMS 10 can be used to predict fetal outcomes either: (1) for births that might occur at the time of prediction; or (2) for births that might occur at some predetermined time in the future (e.g., twenty minutes) after the prediction. Alternatively, although not specifically addressed herein, the teachings of the present invention could be adapted to predict many other types of patient outcomes based on current data.

The OIMS 12 preferably includes, among other things, a transducer (not shown) for converting uterine contractions of the mother to electrical signals, as well as a transducer (not shown) for measuring the heart rate of the fetus inside the mother. The FHR and UC data in the form of electrical signals are passed along an RS-232 cable 18 from the OIMS 12 to the IFMS 10. Any other suitable means of communication other than an RS-232 cable could also be used. The OIMS 12 may include any suitable system for performing these unctions. Examples of such systems are produced by Hewlett-Packard, Corometrics, Toshiba, General Electric, Siemens, and others. For example, the OIMS 12 may be an HP Series 50 OB TraceVue system, Model No. M1381A, Rev. A.01 with an HP Bedside Monitor, Model No. HP 8440A, available from Hewlett-Packard, or any other suitable system.

As is also shown in FIG. 1, the IFMS 10 can be implemented in any suitable processor such as a personal computer. An example of such a suitable computer is any PC-based computer having the following minimum system specifications: Pentium II processor or equivalent, operating at 300 MHz.; 128 Megabytes of RAM; 2 Gigabytes of disk drive storage; an RS-232 serial port; a 2-D graphics accelerator; and Windows NT software, version 4.0. Any PC meeting the preceding specifications or better should serve as a sufficient platform for the IFMS 10. As PCs with higher speed, greater capacity, and other improved capabilities continue to become available, it may be preferable to implement the IFMS 10 in such improved PCs.

The data processing performed by the IFMS 10 can be seen to be divisible into several different functional blocks, as shown in FIG. 2. The IFMS includes seven components, grouped into three layers: the top layer is the learning/supervisory level of the system, the intermediate layer is the system adaptation level, and the bottom layer is the analysis and evaluation level which performs the result analysis, explanation, display and system evaluation functions.

During patient monitoring, the new FHR and UC input received from the OIMS 12 will enter the Case-Base 20 for data preprocessing (i.e., formatting and noise filtering). The Case-Based Reasoning block 22 will then perform case-based reasoning, based on a priori knowledge stored in the Case-Base 20 and patient information, to select an appropriate existing case for use in fetal signal analysis, FHR and UC features extraction and selection, and for fetal outcome prediction. The selected case will dictate a specific data extension mode to be performed by Data Extension block 24, and a specific set of FHR and UC features to be extracted from the input data by the Features Extraction and Selection block 26. These features will be used by the Outcome Prediction block 28 to accurately predict fetal outcome. The outcome prediction result will be analyzed, explained and displayed on the terminal screen of the IFMS 10. It will also be evaluated by the Result Analysis, In. Explanation, Display and Evaluation block 30. The system performance evaluation result will be used by the Rule-Base Adjustment block 32 for rule-base adjustment so that the next fetal outcome prediction for similar case will be better. Finally, the knowledge-base 20 will be updated with new/enhanced fuzzy models under the coordination of the Case-Based Reasoning block 22.

Following is a detailed description for each processing block.

1. Case-Base:

The Case-Base block 20 includes a knowledge-base and a Case-Based Management System (CBMS). The knowledge-base is a data-base containing two types of information. The first type of information is patient biographical data which is grouped into various cases. The biographical data could include any of various types of data, such as gender (male/female), gestational age (e.g., less than or above 40 weeks, or relative to some other age), medication (normal, diabetic, hypertension, narcotic. Etc.), and fetal outcome including arterial cord blood gas base-excess (CG-artery-BE) and arterial cord blood gas pH (CG-artery-pH). The second type of information is an optimal set of features which uniquely characterizes the dynamic behavior of the patient FHR and UC responses, and the fuzzy relationship (i.e., fuzzy model) between these features and the fetal outcome for each case. These fuzzy models were derived from patient data during system training/learning. The CBMS was developed to allow an efficient case information storage and retrieval, quick model access, and automatic data analysis for accurate outcome prediction.

2. Case-Based Reasoning:

The main function of the Case-Based Reasoning block 22 is the selection of an appropriate case and its corresponding fuzzy model for fetal outcome prediction. This type of reasoning is used to assign a patient to one of the existing cases in the case-base, if there is a match (i.e., high correlation) between the characteristic features derived from the FHR and UC input and the ones in the case-base; or to generate a new case. When there is a match, the fuzzy model derived for this case during system training will be used for outcome prediction. If a new case has to be generated, the fuzzy model of the closest case (i.e., case having highest correlation with the input features) will be used as a starting model for outcome prediction after some adjustments.

Model adjustment is done iteratively by the Rule-Base Adjustment block 32 through a learning algorithm to minimize the outcome prediction error.

3. Data Extension:

The IFMS has the capability of providing 20-minute forward data extension so that clinicians may assess current and/or predicted fetal status and balance his/her decision properly. This function is performed by the Data Extension block 24 which uses on-line structure adjustment and weight learning adaptation algorithms of the Volterra Polynomial Basis Function (VPBF) network for dynamic data prediction.

Consider the nonlinear discrete system described by:

$$X_{t+1}=G(X_t, u_t) \quad y_t=h(X_t, u_t) \tag{1}$$

where G(.) is a nonlinear function vector, h(.) a nonlinear function, $X_t$ the state vector, $y_t$ the output, and $u_t$ the input. On the basis of the input and output relation of a system, the above nonlinear discrete system can also be expressed by a NARMA (Nonlinear Auto-Regressive Moving Average) model:

$$y_t=f(y_{t-1}, y_{t-2}, \ldots, y_{t-n}, u_{t-1}, u_{t-2}, \ldots, u_{t-m}) \tag{2}$$

where f(.) is some nonlinear function, n and m are the corresponding maximum delays.

The nonlinear function f(.) in the NARMA model can be approximated by a single-layer neural network. This includes a linear combination of basis functions $$f*(xt) = \sum_{k=1}^{N} wk\phi k(xt) \tag{3}$$

where $x_t=[y_{t-1}, y_{t-2}, \ldots, y_{t-n}, u_{t-1}, u_{t-2}, \ldots, u_{t-m}]$, $\phi_k(x_t)$ is the basis function and $w_k$ the weight.

Using Volterra polynomials as the basis functions, the representation of the nonlinear function $f(x_t)$ is then given by:

$$f^*(x_t) = w_1 + w_2 y_{t-1} + w_3 y_{t-2} + \ldots + w_{n+1} y_{t-n}$$
$$+ w_{+2} u_{t-1} + \ldots + w_{n+m+1} u_{t-m}$$
$$+ w_{n+m+2} y_{t-1}^2 + w_{n+m+3} y_{t-1} y_{t-2} + \ldots w_N u_{t-m}^l \cdot {}_{mN}$$
$$= \Sigma w_k \phi_k(x_t)_{k=1} \quad (4)$$

where $$[\phi_1, \phi_2, \phi_3, \ldots, \phi_{n+1}, \phi_{n+2}, \ldots, \phi_{n+m+1}, \phi_{n+m+2}, \phi_{n+m+3}, \ldots, \phi_N](X_t)$$
$$= [1, y_{t-1}, y_{t-2}, \ldots, y_{t-m}, u_{t-1}, \ldots, u_{t-m}, y_{t-1}^2, y_{t-1} y_{t-2}, \ldots, u_{t-m}^l] \quad (5)$$

$$N = (n+m+l)!/[l!(n+m)!] \quad (6)$$

is the set of the Volterra polynomial basis functions.

Increasing the order l, the number N of basis functions becomes larger and larger.

The IFMS estimates the function $f^*(x_t)$ using a proper-sized neural network so that the approximation accuracy is within the required bound.

The estimated function $f^*(x_t)$ in the NARMA model can also be expressed by $$f^*(x_t) = W_{t-1}^T \Phi_{t-1} \quad (7)$$

where the weight vector $W_{t-1}$ and the basis function vector $\Phi_{t-1}$ are $$W_{t-1} = [w_1(t-1) \ w_2(t-1) \ \ldots \ w_L(t-1)]^T \quad (8)$$

$$\Phi_{t-1} = [\phi_1^\circ(x_t) \ \phi_2^\circ(x_t) \ \ldots \ \phi_L^\circ(x_t)]^T \quad (9)$$

and the initial weight vector is $W_o = [w_1^\circ \ w_2^\circ \ \ldots \ w_L^\circ]^T$.

Let $y_t$ be the system output. The estimation problem is then to find a vector W belonging to the set defined by $$\Xi(W) = \{W : |y_t - W^T \Phi_{t-1}| \leq \delta_L, \forall t \in N^+\}. \quad (10)$$

A recursive weight learning algorithm for the VPBF network is as follows:

$$W_t = W_t' - \alpha_t \beta_t \eta_t P_t \Phi_{t-1} e_t \quad (11)$$

$$W_t' = W_{t-1} + \alpha_t \beta_t P_t \Phi_{t-1} e_t \quad (12)$$

$$P_t = P_{t-1} - \beta_t \gamma_t P_{t-1} \Phi_{t-1} \Phi_{t-1}^T P_{t-1} \quad (13)$$

$$e_t = y_t - W_{t-1}^T \Phi_{t-1} \quad (14)$$

$$\alpha_t = (1 - \delta |e_t|^{-1})(1 + \Phi_{t-1}^T P_{t-1} \Phi_{t-1})^{-1} \quad (15)$$

$$\beta_1 = \begin{cases} 1, & |e_t| > \delta \\ 0, & |e_t| \leq \delta \end{cases} \quad (16)$$

$$\gamma_t = (|e_t| - \delta)(|e_t| + (2|e_t| - \delta)\Phi_{t-1}^T P_{t-1} \Phi_{t-1})^{-1} \quad (17)$$

$$\eta_t \in \begin{cases} 0, & \|W_t'\|_2 \leq M \\ [s^-, s^+], & \|W_t'\|_2 > M \end{cases} \quad (18)$$

where the lower and upper bounds of $\eta_t$ are given by $$s^- = 1 + (\alpha_t e_t \Phi_{t-1}^T P_t W_{t-1} - c_t) / \|\alpha_t e_t P_t \Phi_{t-1}\|_2^2 \quad (19)$$

$$s^+ = 1 + (\alpha_t e_t \Phi_{t-1}^T P_t W_{t-1} + c_t) / \|\alpha_t e_t P_t \Phi_{t-1}\|_2^2 \quad (20)$$

where $$c_t = \sqrt{(\alpha_t e_t \Phi_{t-1}^T P_t W_{t-1})^2 + \|\alpha_t e_t P_t \Phi_{t-1}\|_2^2 (M^2 - \|W_{t-1}\|_2^2)} \quad (21)$$

M is the upper bound of the 2-norm of the weight vector $W_t$, and $\delta$ is the desired approximation error.

The IFMS 10 displays the 20-min extension of the FHR & UC tracings in a separated window, with features enhanced by different colors. This option will be activated by a button on the main screen menu.

4. Features Extraction and Selection:

The function of the Feature Extraction and Selection block 26 includes extracting and selecting an appropriate set of fetal heart rate (FHR) features and uterine contraction (UC) features for proper characterizing patient characteristics. The features that will be automatically generated by the IFMS 10 include traditional features and new features.

Some of the traditional features for FHR include:

Baseline FHR: compiled over 5 minutes.

Beat-to-beat variability: compiled over 5 minutes.

Ten-second variability: compiled over 10 seconds: 30 such distributions combined to give one value for each 5 minutes.

One-minute variability: compiled over 1 minute: 5 such distributions combined to give one value for each 5 minutes.

Number of accelerations of $\geq 10$ bpm for $\geq 15$ seconds: number in 5 minutes.

Number of accelerations of $\geq 15$ bpm for $\geq 15$ seconds: number in 5 minutes.

Number of decelerations of $\geq 10$ bpm for $\geq 60$ seconds: number in 5 minutes.

Deceleration duration: average of all in 5 minutes.

Deceleration depth: average of all in 5 minutes.

Contraction number: number in 5 minutes

Contraction area (for one cycle): average of all in 5 minutes.

There are also new features derived from the scale-space domain.

The actual features used may be the entire set, or a subset, of the preceding features. Alternatively, additional features may be used. The actual features used will be automatically selected by the system.

First, a gaussian convolution is used as a primitive scale-parameterization, as shown in FIG. 5. The gaussian convolution of a signal f(x) depends both on x, the signal's independent variable, and on $\sigma$, the gaussian's standard deviation. The convolution is given by:

$$F(x,\sigma) = f(x) * g(x,\sigma) = \int_{-\infty}^{\infty} f(u)(1/\sigma\sqrt{(2\pi)}) \exp\{-(x-u)^2/(2\sigma^2)\} du \quad (22)$$

where "*" denotes convolution with respect to x. This function defines a surface on the $(x, \sigma)$-plane, where each profile of constant $\sigma$ is a gaussian-smoothed version of f(x), the amount of smoothing increasing with $\sigma$. We will call the $(x,\sigma)$-plane scale-space, and the function F, defined in (22), the scale-space image of f.

Then, at any given value of $\sigma$, the extrema in the $n^{th}$-derivative of the smoothed signal are given by the zero-crossings in the $(n+1)^{th}$ derivative, computed using the relation:

$$\partial^n F / \partial x^n = f * (\partial^n g / \partial x^n) \quad (23)$$

where the derivatives of the gaussian are readily obtained. In terms of the scale-space image, the inflections at all values of $\sigma$ are the points that satisfy $$F_{xx}=0 F_{xxx} \neq 0 \quad (24)$$

Using subscript notation to indicate partial differentiation. As shown in FIG. 6, the contours of $F_{xx}=0$ mark the appearance and motion of inflection points in the smoothed signal, and provide the raw material for a qualitative description over all scales, in terms of inflection points.

Finally, the scale-space image is reduced to a simple interval tree, as shown in FIG. 7, concisely but completely describing the qualitative structure of the signal over all scales of observation. This simplification rests on the basic property of the scale-space image: as σ is varied, extremal points in the smoothed signal appear and disappear at singular points (the tops of the arches). Passing through such a point with decreasing a, σ pair of extrema of opposite sign appear in the smoothed signal. At these points, and only these points, the undistinguished interval in the which the singularity occurs splits into three subintervals. In general, each undistinguished interval, observed in scale-space, is bounded on each side by the zero contours that define it, bounded above by the singular point at which it merges into an enclosing interval, and bounded below by the singular point at which it divides into sub-intervals. Consequently, to each interval I corresponds a node in a tree, whose parent node denotes the larger interval from which I merged, and whose offspring represent the smaller intervals into which I subdivide. Each interval also defines a rectangle in scale-space, denoting its location and extent on the signal and its location and extent on the scale dimension. Collectively, these rectangles tesselate the (x,σ)-plane. The interval tree may be viewed in two ways: as describing the signal simultaneously at all scales, or as generating a family of single-scale descriptions, each defined by a subset of nodes in the tree that cover the x-axis. The interval tree seems to be flexible enough to capture human perceptual intuitions. It was used to extract scale-space features related to FHR accelerations and decelerations.

Since the number of features derived from the FHR and UC tracings are numerous, only the most contributing features are selected to build the fuzzy model for fetal outcome prediction for each case. In the IFMS, the feature selection task is done through a special clustering algorithm which determines a cluster-specific contribution of each feature to the variance of the data. The contribution weight of a feature is proportional to the deviation (squared) of the feature's within-cluster mean from its grand mean. The more deviant a feature is from a standard (the grand mean, in this case), the more interesting it is. Each contribution weight is a part of clustering criterion to be maximized, not a posterior quality measure. A "separate-and-conquer" version of the K-Means clustering method produces clusters one by one, not simultaneously, and relaxes the problem of defining a partition size in advance. The features with greatest contribution towards a cluster (or cluster structure) were used to generate a fuzzy model that approximately describes the behavior of the data subset within the cluster.

5. Outcome Prediction:

The Outcome Prediction block 28 uses the selected/adjusted fuzzy model to predict fetal outcome. The fuzzy model used by the IFMS 10 is a multi-input single-output (MISO) linguistic model of Takagi-Sugeno type to represent the fuzzy relationship between the input features and fetal outcome:

IF $u_1$ is $B_{i1}$ AND . . . AND $u_r$ is $B_{ir}$ THEN $y_i=b_{i0}+b_{i1}u_1+ \ldots +b_{ir}u_r, i=(1,m)$ (25)

assuming that the fuzzy model has m rules. The crisp output inferred by this fuzzy model according to the Min-Max method of fuzzy reasoning is $$y = \left[\sum_{i=1}^{m} \tau_i y_i^*\right] / \left[\sum_{i=1}^{m} \tau_i\right] \quad (26)$$

where $y_i^*$ denotes the predicted outcome based on the ith fuzzy rule, and $\tau_i$, i=(1,m) are the degrees of firing (DOF) of the rules:

$$\tau_i = B_{s1}(u_1)\hat{}B_{i2}(u_2)\hat{} \ldots \hat{}B_{ir}(u_r) \quad (27)$$

for given crisp input values $u_1, u_2, \ldots, u_r$.

To obtain an analytical expression of the transformation input-output we replace the min operator in (27) by the product and, in addition, assume that the reference antecedent fuzzy sets are defined by Gaussian membership functions:

$$B_{ij}(u_j)=\exp\{-\frac{1}{2}[(u_j-x_{ij}^*)/\sigma_{ij}]^2\} \quad (28)$$

with parameters $x_{ij}^*$ and $\sigma_{ij}$. Then we obtain the following expression for the DOF of the ith rule:

$$\tau_i = B_{i1}(u_1).B_{i2}(u_2) \ldots B_{ir}(u_r)$$

$$\tau_i = B_{i1}(u_1) \cdot B_{i2}(u_2) \ldots B_{ir}(u_r) \quad (29)$$

$$= \prod_{j=1}^{r} \left(\exp\{-1/2[(u_j - x_{ij}^*)/\sigma_{ij}]^2\}\right)$$

$$= \exp\left\{-1/2 \sum_{j=1}^{r} [(u_j - x_{ij}^*)/\sigma_{ij}]^2\right\}$$

By substitution of (29) into (26) we obtain an expression for the crisp output of the linguistic model that is determined by the parameters of the antecedent and consequent fuzzy sets $y_i^*$, $x_{ij}^*$, and $\sigma_{ij}$, i=(1,m), j=(1,r):

$$y = \frac{\sum_{i=1}^{m} \tau_i y_i^*}{\sum_{i=1}^{m} \tau_i} = \frac{\sum_{i=1}^{m} y_i^* \left(\exp\left\{-1/2 \sum_{j=1}^{r} [(u_j - x_{ij}^*)/\sigma_{ij}]^2\right\}\right)}{\sum_{i=1}^{m} \left(\exp\left\{-1/2 \sum_{j=1}^{r} [(u_j - x_{ij}^*)/\sigma_{ij}]^2\right\}\right)} = \sum_{i=1}^{m} v_i y_i^* \quad (30)$$

where $v_i$, i=(1,m) are the normalized DOF of the individual rules:

$$v_i = \frac{\tau_i}{\sum_{k=1}^{m} \tau_k} = \frac{\exp\left\{-1/2 \sum_{j=1}^{r} [(u_j - x_{ij}^*)/\sigma_{ij}]^2\right\}}{\sum_{k=1}^{m} \left(\exp\left\{-1/2 \sum_{j=1}^{r} [(u_j - x_{kj}^*)/\sigma_{kj}]^2\right\}\right)} \quad (31)$$

Using (30) we can represent the linguistic model (25) as a three-layer network as shown in FIG. 3. The output of this model will then be given by:

$$y = \left\{\sum_{i=1}^{m} \tau_i(b_{i0} + b_{i1}u_1 + \ldots + b_{ir}u_r)\right\} / \left\{\sum_{i=1}^{m} \tau_i\right\} \quad (32)$$

-continued $$= \frac{\sum_{i=1}^{m}\left(\exp\left\{-1/2\sum_{j=1}^{r}[(u_j-x_{ij}^*)/\sigma_{ij}]^2\right\}\right)(b_{i0}+b_{i1}u_1+\ldots+b_{ir}u_r)}{\sum_{i=1}^{m}\left(\exp\left\{-1/2\sum_{j=1}^{r}[(u_j-x_{ij}^*)/\sigma_{ij}]^2\right\}\right)}$$

6. Result Analysis, Explanation, Display and Evaluation:

Based on the predicted outcome from the Outcome Prediction block 28, the Analysis, Explanation, Display and Evaluation block 30 will use a rule set to explain the behavior of the fetus. This explanation may take any of several forms, including acoustic or visual forms. For example, one of the following statements may be displayed in the "Advice window" on the terminal screen:

"No evidence of fetal distress."
"Further evaluation may be necessary."
"Non-reassurring tracing."

Other statements or alarms could also be provided for the user.

The Display function of this block also provides a full display capability for the user to review the FHR and UC input tracings, with color enhancement of various extracted features for ease of information assessment.

Another function performed by the Analysis, Explanation, Display and Evaluation block 30 is the evaluation of outcome prediction performance of the Outcome Prediction block 28. It uses an outcome prediction error measure to assess the prediction accuracy and guides the IFMS system tuning during the system learning and training phase with known data sets.

7. Rule-Base Adjustment:

The learning algorithm for a multi-input single-output (MISO) linguistic model (22) was derived as follows. For a given collection of crisp input-output data $(u_{1k}, u_{2k}, \ldots, u_{rk})$, $k=(1,K)$, we can formulate the model parameter estimation problem as a minimization of the square of chi instantaneous errors between the output y of the fuzzy model (22) and the current output reading $y_k$ with respect to the unknown parameters:

$$E_k = \frac{1}{2}(y-y_k)^2 = \frac{1}{2}e^2 \quad (33)$$

We then obtain the following rules for back-propagation learning for fuzzy model adjustment:

$$b_{i0}(k+1)=b_{i0}(k)-\alpha(\partial E_k/\partial b_{i0})=b_{i0}(k)-\alpha v_i e \quad (34)$$

$$b_{ij}(k+1)=b_{ij}(k)-\alpha(\partial E_k/\partial b_{ij})=b_{ij}(k)-\alpha v_i e u_j, \, j=(1,r) \quad (35)$$

$$x_{ij}^*(k+1)=x_{ij}^*(k)-\alpha(\partial E_k/\partial x_{ij})=x_{ij}^*(k)-\alpha v_i(b_{i0}+b_{i1}u_1+\ldots+b_{ir}u_r-y)e[(u_j-x_{ij}^*(k))/\sigma_{ij}^2(k)] \quad (36)$$

$$\sigma_{ij}(k+1)=\sigma_{ij}(k)-\alpha(\partial Ek/\partial \sigma_{ij})=\sigma_{ij}(k)-\alpha v_i(b_{i0}+b_{i1}u_1+\ldots+b_{ir}u_r-y)e[(u_j-x_{ij}^*(k))^2/\sigma_{ij}^3(k)] \quad (37)$$

where $\alpha>0$ is the learning rate.

The bloc-diagram of the learning algorithm, combining with the three-layer neural network is shown in FIG. 4. The parameter updating process stops when $\Delta y_i^*$, $\Delta x_{ij}^*$, and $\Delta \sigma_{ij}$ are sufficiently small (i.e., less than a pre-specified threshold).

In the forward pass, we calculate the current DOF of the rules, the $\tau_i$'s and their normalized values $v_i$'s, and the estimated output of the fuzzy model y; current estimates $y_j^*(k)$, $x_{ij}^*(k)$, and $\sigma_{ij}(k)$ are used in this calculation. In the backward pass, the current parameter estimates $y_i^*(k)$, $x_{ij}^*(k)$ and $\sigma_{ij}(k)$ are updated according to the learning rules (34), (35), (36), and (37) with rates:

$$\Delta y_i^*=-\alpha v_i e; \, \Delta x_{ij}^*=-v_i e(y_i^*-y)[(u_j-x_{ij}^*(k))/\sigma_{ij}^2(k)]; \, \Delta \sigma_{ij}=-\alpha v_i e(y_i^*-y)[(u_j-x_{ij}^*(k))^2/\sigma_{ij}^3(k)] \quad (38)$$

where $y_i^*$ is given by:

$$y_i^*=b_{i0}+b_{i1}u_1+\ldots+b_{ir}u_r. \quad (39)$$

All of the above data processing is performed by a computer as described above. As currently being developed, the computer has been programmed in the $C^{++}$ programming language. Alternatively, the computer could be programmed in some other suitable programming language, or all or portions of the data processing functions could be implemented in hardware.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

The invention claimed is:

1. A method of automatically providing an output representative of the health of a fetus carried by a mother, based on fetal and maternal data, with a computer-based predictor, the method comprising:
   receiving biographical data about the fetus and the mother;
   categorizing the fetal and maternal data combination as one of a plurality of types of cases based on the biographical data;
   receiving physical data about the current condition of the fetus and the mother;
   processing the physical data to extract characteristic features;
   selecting a subset of the characteristic features based on the type of case that the fetal and maternal data combination has been categorized as; and
   providing an output representative of the health of the fetus from the subset of characteristic features based on previously-developed fuzzy relationships between fetal and maternal data and fetal health.

2. A method as defined in claim 1, further including communicating the output to a user.

3. A method as defined in claim 1, wherein the provided output is representative of the current status of the fetus.

4. A method as defined in claim 1, wherein the provided output is representative of the health of the fetus at a predetermined time in the future.

5. A method as defined in claim 4, wherein the predetermined time is approximately twenty minutes after the output is reported.

6. A method as defined in claim 1, further including developing fuzzy relationships between fetal and maternal data and fetal health based on data and known fetal health from past pregnancies and births.

7. A method as defined in claim 1, further including using the reported fetal health to adjust and optimize the selecting operation.

8. A method as defined in claim 1, further including using the reported fetal health to adjust and optimize the providing operation.

9. A method as defined in claim 1, wherein the received physical data includes fetal heart rate and uterine contraction data.

10. A method as defined in claim 1, wherein the received biographical data includes fetal gender, gestational age, and medication data.

11. A method as defined in claim 1, wherein the categorizing operation includes case-based reasoning.

12. A method as defined in claim 1, wherein the extracted characteristic features in the processing operation include features relating to the variability in the heart rate of the fetus.

13. A method as defined in claim 1, wherein the extracted characteristic features in the processing operation include features relating to the accelerations in the heart rate of the fetus.

14. A method as defined in claim 1, wherein the extracted characteristic features in the processing operation include features relating to the decelerations in the heart rate of the fetus.

15. A method as defined in claim 1, wherein the extracted characteristic features in the processing operation include features relating to the uterine contractions by the mother in a predetermined period of time.

16. A method of automatically reporting fetal health for a fetus carried by a mother, based on fetal and maternal data, with a computer-based assessor, the method comprising:
receiving fetal and maternal data;
processing the fetal and maternal data to generate and select an optimal set of fetal and maternal features; and
applying the optimal selected set of fetal and maternal features to the assessor to assess and predict fetal health based on identified fuzzy relationships between fetal and maternal data and fetal health;
further including a case-based reasoning processor that receives biographical data about the fetus and the mother and, using case-based reasoning, determines the optimal set of data features to be applied to the assessor.

17. A system for automatically assessing fetal health and predicting fetal outcomes based on fetal and maternal data, comprising:
a transducer for converting a physical condition of a fetus or mother to a signal representative thereof;
a processor for converting the signal to a set of signal features, the set of features being based in part on fetal and maternal biographical data; and
an assessor receptive of the processed signal features for assessing fetal health and predicting fetal outcome based on identified fuzzy relationships between fetal and maternal data and fetal outcomes;
further including a case-based reasoning processor that receives biographical data about the fetus and the mother and, using case-based reasoning, determines the optimal set of data features to be applied to the assessor.

18. A method as defined in claim 17, wherein the optimal set of features is selected based on a learning process that allows the assessor to categorize the fetal and maternal data as belonging to one of a plurality of types of cases and to select the optimal set of features from a larger set of features based on the case type.

19. A system as defined in claim 11, wherein the processor converts the signal to an optimal set of signal features, the optimal set of features being selected based on a learning process that allows the assessor to categorize the fetal and maternal data as belonging to one of a plurality of types of cases and to select the optimal set of features from a larger set of features based on the case type.

20. A method for automatically predicting the future health of a particular person based on present data about the person, the method comprising:
automatically developing inference rules based on known data about persons and known data about the future health of those same persons;
receiving physical data about the present status of a particular person;
automatically processing the received data to generate a set of characteristic features; and
applying the inference rules to the derived characteristic features to predict the future health of the particular person.

21. A system for automatically providing an output representative of the health of a fetus carried by a mother, based on fetal and maternal data, with a computer-based predictor, comprising:
means for receiving biographical data about the fetus and the mother;
means for categorizing the fetal and maternal data combination as one of a plurality of types of cases based on the biographical data;
means for receiving physical data about the current condition of the fetus and the mother;
means for processing the physical data to extract characteristic features;
means for selecting a subset of the characteristic features based on the type of case that the fetal and maternal data combination has been categorized as; and
means for providing an output representative of the health of the fetus from the subset of characteristic features based on previously-developed fuzzy relationships between fetal and maternal data and fetal health.

22. A system as defined in claim 21, further including means for communicating the output to a user.

23. A system as defined in claim 21, wherein the provided output is representative of the current status of the fetus.

24. A system as defined in claim 21, wherein the provided output is representative of the health of the fetus at a predetermined time in the future.

25. A system as defined in claim 21, wherein the predetermined time is approximately twenty minutes after the output is reported.

26. A system as defined in claim 21, further including means for developing fuzzy relationships between fetal and maternal data and fetal health based on data and known fetal health from past pregnancies and births.

27. A system as defined in claim 21, further including means for using the reported fetal health to adjust and optimize the selecting operation.

28. A system as defined in claim 21, further including means for using the reported fetal health to adjust and optimize the providing operation.

29. A system as defined in claim 21, wherein the received physical data includes fetal heart rate and uterine contraction data.

30. A system as defined in claim 21, wherein the received biographical data includes fetal gender, gestational age, and medication data.

31. A system as defined in claim 21, wherein the means for categorizing utilizes case-based reasoning.

32. A system as defined in claim 21, wherein the extracted characteristic features include features relating to the variability in the heart rate of the fetus.

33. A system as defined in claim 21, wherein the extracted characteristic features include features relating to the accelerations in the heart rate of the fetus.

34. A system as defined in claim 21, wherein the extracted characteristic features include features relating to the decelerations in the heart rate of the fetus.

35. A system as defined in claim 21, wherein the extracted characteristic features include features relating to the uterine contractions by the mother in a predetermined period of time.

36. A system for automatically reporting fetal health for a fetus caried by a mother, based on fetal and maternal data, with a computer-based assessor, comprising means for receiving fetal and maternal data;

means for processing the fetal and maternal data to generate and select an optimal set of fetal and maternal features; and means for applying the optimal selected set of fetal and maternal features to the assessor to assess and predict fetal health based on identified fuzzy relationships between fetal and maternal data and fetal health;

further including a case-based reasoning processor that receives biograhical data about the fetus and the mother and, using case-based reasoning, determines the optimal set of data features to be applied to the assessor.

37. A method as defined in claim 36, wherein the optimal set of features is selected based on a learning process that allows the assessor to categorize the fetal and maternal data as belonging to one of a plurality of types of cases and to select the optimal set of features from a larger set of features based on the case type.

* * * * *

UNITED STATES PATENT AND TRADEMARK OFFICE
CERTIFICATE OF CORRECTION

PATENT NO. : 6,254,537 B1
DATED : July 3, 2001
INVENTOR(S) : Duong Nguyen

It is certified that error appears in the above-identified patent and that said Letters Patent is hereby corrected as shown below:

Column 1,
Line 4, add the sentence:
-- This invention was made with government support under 5 R44 HD 31837-03 awarded by the National Institute of Child Health and Human Development. The government has certain rights in the invention. --

Signed and Sealed this

Sixteenth Day of April, 2002

Attest:

Attesting Officer

JAMES E. ROGAN
*Director of the United States Patent and Trademark Office*